United States Patent [19]

Denton

[11] Patent Number: 5,103,684
[45] Date of Patent: Apr. 14, 1992

[54] MATERIAL CUTTING TOOL
[75] Inventor: Duane N. Denton, Ogden, Utah
[73] Assignee: The United States of America as represented by the Secretary of the Air Force, Washington, D.C.
[21] Appl. No.: 711,126
[22] Filed: Jun. 6, 1991

Related U.S. Application Data
[63] Continuation of Ser. No. 533,240, May 30, 1990, abandoned.

[51] Int. Cl.[5] ............................................. G01N 1/04
[52] U.S. Cl. .................................... 73/864.41; 30/301
[58] Field of Search ..................... 73/864.41, 864.44; 83/919; 30/380, 501, 502, 169, 172, 278, 279.2, 296.1, 320, 329, 121, 301, 316

[56] References Cited

U.S. PATENT DOCUMENTS

| | | | |
|---|---|---|---|
| 509,899 | 12/1893 | Heysinger | 30/279.2 |
| 841,332 | 1/1907 | Lehnert | 30/169 |
| 895,097 | 8/1908 | Lucas | 30/169 |
| 1,437,624 | 12/1922 | Tyler | 30/320 |
| 1,818,398 | 8/1931 | Huxford | 30/121 |
| 2,236,323 | 3/1941 | Stachowiak | 30/320 |
| 2,505,917 | 5/1950 | Schumacher | 30/278 |
| 2,783,537 | 3/1957 | Gringer | 30/320 |
| 4,541,757 | 9/1985 | Reynolds et al. | 407/53 |
| 4,585,600 | 4/1986 | Rollyson et al. | 264/3.3 |
| 4,761,254 | 8/1988 | Olliff | 264/3.3 |
| 4,766,799 | 8/1988 | Olliff | 86/45 |

FOREIGN PATENT DOCUMENTS

| | | | |
|---|---|---|---|
| 486469 | 9/1952 | Canada | 30/169 |
| 805226 | 11/1936 | France | 30/356 |

Primary Examiner—Robert Raevis
Attorney, Agent, or Firm—Thomas C. Stover; Donald J. Singer

[57] ABSTRACT

A safe cutting tool for cutting and undercutting samples of solid material e.g., from solid rocket propellant wherein a blade curves sidewise around an opening to define a sleeve, the edges of which are opposed cutting edges which bevel into the opening from each opposed outside edge. The tool is employed in cutting channels in solid material and can be mounted on a handle, either in axial alignment therewith or at an angle thereto for undercutting purposes. The tool can be employed for excising a sample of solid material e.g., by cutting channels therearound and then undercutting such sample to free same. During cutting, shavings or cuttings of the material pass up the beveled blade and through the opening in the cutting tool sleeve, which cutting can then be grasped and removed by the operator. Such cutting tool, with rounded cutting head and opposed interior directed cutting blades, cuts through solid materials with reduced effort and increased speed and cuts on back and forth strokes, with reduced scrap waste and reduced dust for improved safety, e.g., when cutting explosive propellant material. The tool is particularly useful and has the above attributes in the undercutting of solid material including rocket propellant.

14 Claims, 4 Drawing Sheets

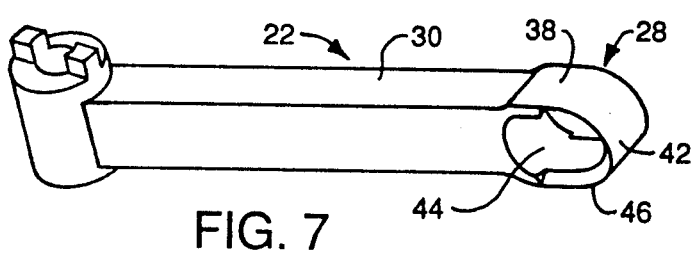
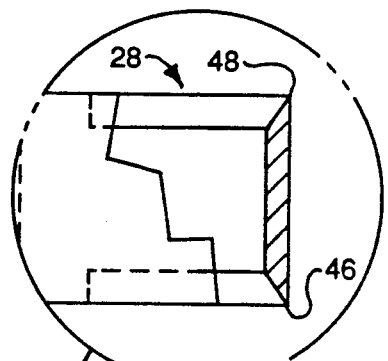
FIG. 7
FIG. 9A
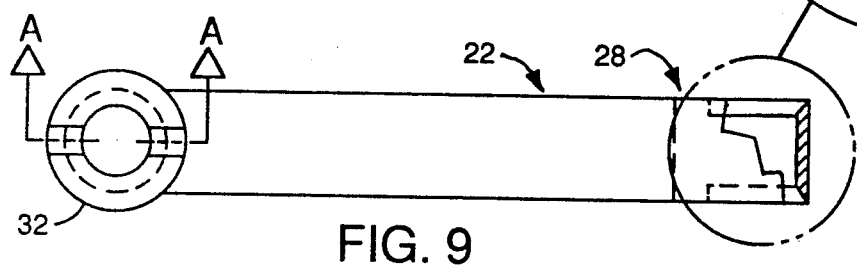
FIG. 9
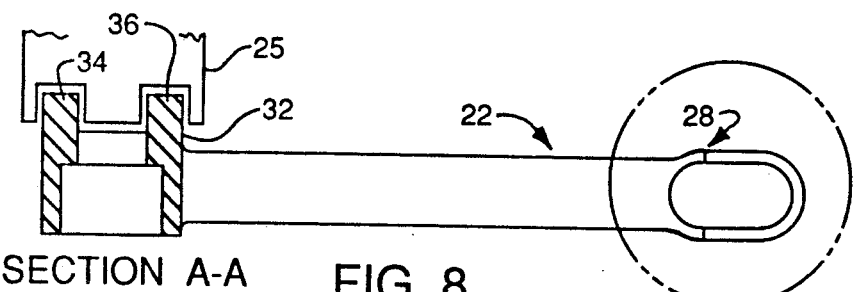
SECTION A-A    FIG. 8
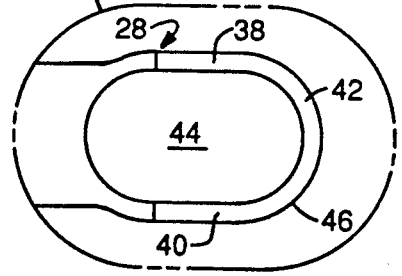
FIG. 8A
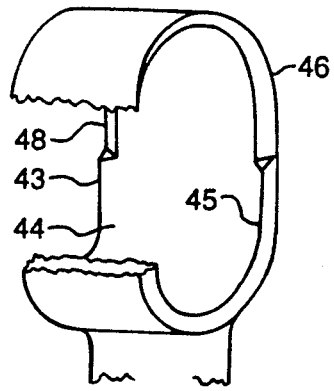
FIG. 10
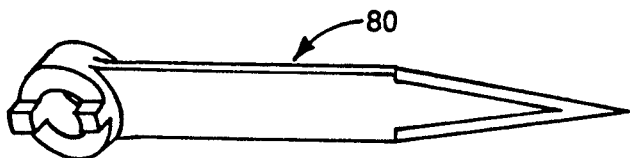
FIG. 11

1

MATERIAL CUTTING TOOL

STATEMENT OF GOVERNMENT INTEREST

The invention described herein may be manufactured and used by or for the Government for governmental purposes without the payment of any royalty thereon.

RELATED APPLICATIONS

This is an FW Continuation application of application Ser. No. 07/533,240, filed May 30, 1990, having the same title, now abandoned.

BACKGROUND OF THE INVENTION

1. Field of the Invention

This invention relates to a tool for cutting material particularly a tool for cutting out samples of material.

1. The Prior Art

Cutting solid material, including abrasive solid material e.g., solid rocket fuel presents several problems. For example, solid rocket fuel or propellant can be in the shape of a hollow cylinder which is mounted inside a plastic liner material, mounted in turn, inside a metal casing. If one wish to remove a sample of such fuel for testing, one can only cut the propellant from the inside so as to avoid cutting into the metal rocket housing or casing.

To cut out a test sample of such propellant, one must cut channels around such sample and then undercut the so-excavated sample to remove same. A suitable test sample size, is e.g. 2 in. by 2 in. by 15 in.

In the past, such samples have been excised using common knifes or saw blades, straight or bent as shown, for example, in FIG. 1. Such make-shift tools have been highly inefficient and ineffective and have required numerous manhours. Such tools have also caused numerous propellant cuttings and waste along with highly inflammable or explosive propellant dust. Accordingly, the prior art tools have proved laborious, wasteful and unsafe, in excising samples of solid material. In other prior art, a milling cutter for rocket solid propellant includes a cutting arm that is attached at a center location to a rotatable arbor, as disclosed in U.S. Pat. No. 4,541,757 to Reynolds (1985). Such cutting tool has an inverted T-shape with a cutting blade laying flat on the bottom of the "T" thereof, connecting to two upstanding vertical blades at the end of the "T", which tool rotates in contact with a block of rocket propellant to cut horizontal and vertical surfaces out of such block as the "T" blades are rotated. Thus steps or indentations can be cut into such blocks but cutting out of fuel samples is not intended nor suggested by this reference. Thus the Reynolds cutting tool is suited for surface shaving or milling operations and uses three blades mounted at right angles to each other.

Accordingly only crude unsuitable or unsafe tools have here-to-fore been available for excising samples of material and there is a need and market for a tool design that overcomes the above prior art short comings.

There has now been discovered a tool for cutting through solid material, which may be operated more quickly and with less effort by an operator, with a pronounced reduction in material shavings and resulting dust than previously possible with prior art tools.

Such tool is safer and less laborious to use and is more productive than cutting tools previously available.

SUMMARY OF THE INVENTION

Broadly the present invention provides a tool for cutting solid material comprising, a handle, a blade mounted to the handle, the blade sides wrapping at least partially around and defining an opening with at least a portion of the cutting edge of the blade pointing generally in the direction of an axis passing through such opening so that upon cutting into the material, a cutting therefrom passes into such opening.

In one embodiment the blade is U-shaped and has a cutting edge that tapers inwardly from the outside edge thereof. In another embodiment, such blade has two opposed beveled edges which taper inwardly from the outside edge thereof, for cutting solid material in two directions.

BRIEF DESCRIPTION OF THE DRAWINGS

The invention will become more apparent from the following detailed specification and drawings in which:

FIG. 7 is a perspective view of a component of the solid material cutting tool embodying the present invention;

FIG. 8 is an elevation plan view partly in section, of the tool component of FIG. 5;

FIG. 8a is an enlarged fragmentary view of a portion of FIG. 8;

FIG. 9 is a plan view of the tool component FIG. 6, taken on lines 7—7, looking in the direction of the arrows;

FIG. 9a is an enlarged fragmentary view of a portion of FIG. 9;

FIG. 10 is a fragmentary perspective view of a portion of the tool component of the invention shown in FIG. 5; and FIG. 11 is a perspective view of another component of the solid material cutting tool embodying the present invention;

DESCRIPTION OF PREFERRED EMBODIMENTS

Figure 2:
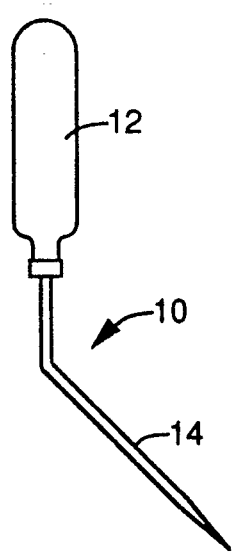
FIG. 2 is an end elevation of the tool of FIG. 1.
Figure 1:
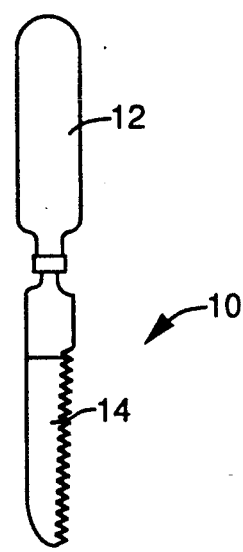
FIG. 1 is an elevation view on a material cutting tool according to the prior art.

Referring now in more detail to the drawings, a cutting tool 10 of the prior art, having handle 12 and saw blade 14, is shown in FIGS. 1 and 2. As noted above, such prior art tool 10 was inefficient, required excessive man hours and generated considerable scrap material and hazardous dust in cutting solid material e.g., solid rocket propellant.

Such prior art tool is replaced by the solid material cutting material cutting on assembly 20 of the present invention, which has cutting tool 22 mounted at an angle to adjustable length handle 24, and is used for cutting solid material e.g., solid rocket propellant 26, as shown or indicated in FIGS. 3, 4, 5 and 6, the operation of which is more fully described below.

The tool 22 has a cutting head 28, a shaft 30 and a handle connecting end 32, as shown in FIGS. 7, 8, 8a, 9 and 9a. The tool 22 connects to handle extension 25 by upstanding nibs 34 and 36, as indicated in FIG. 8.

The cutting head at 28 of the tool 22, has two sides 38 and 40 joined by curved end 42 and defining an elongated, rounded opening 44 therein, as shown in FIGS. 7 and 8. The distance 39 between the outer surfaces of the sides 38 and 40 is the "wrapped width" of the cutting head 28, as shown in FIG. 8.

Preferably the curved end of the cutting head 28, is thicker than the sidewalls 38 and 40, as indicated in FIGS. 8 and 8a, for reasons discussed below.

The edges of the cutting head 28, are beveled or sharpened on both sides, from the outside edges inwardly of the opening (i.e. the inside edges 43 and 45 of the opening 44 per FIG. 10, are in part, filed down, to form outside cutting edges 48 and 46, as shown in FIGS. 7, 8, 9 and 10.

Figure 3:
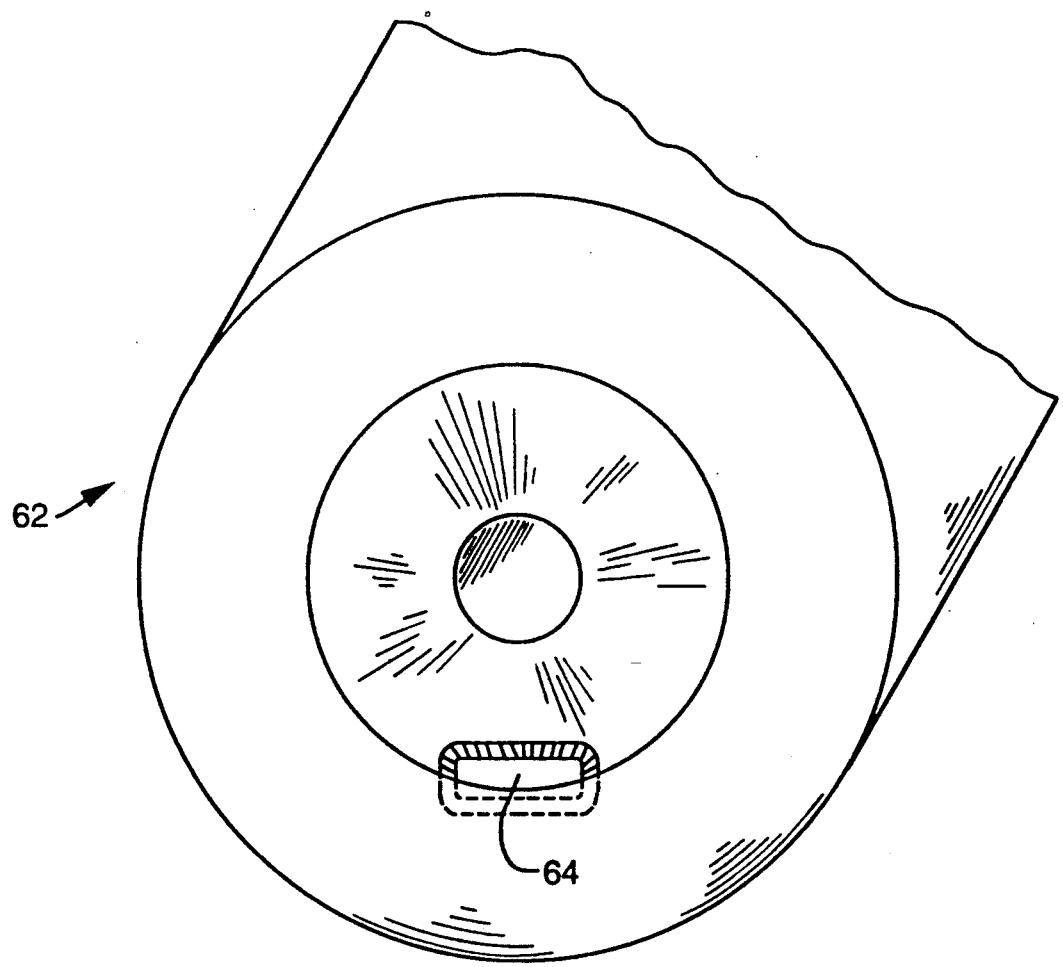
FIG. 3 is a perspective view of a portion of solid material to be cut by the tool embodying the present invention.
Figure 4:
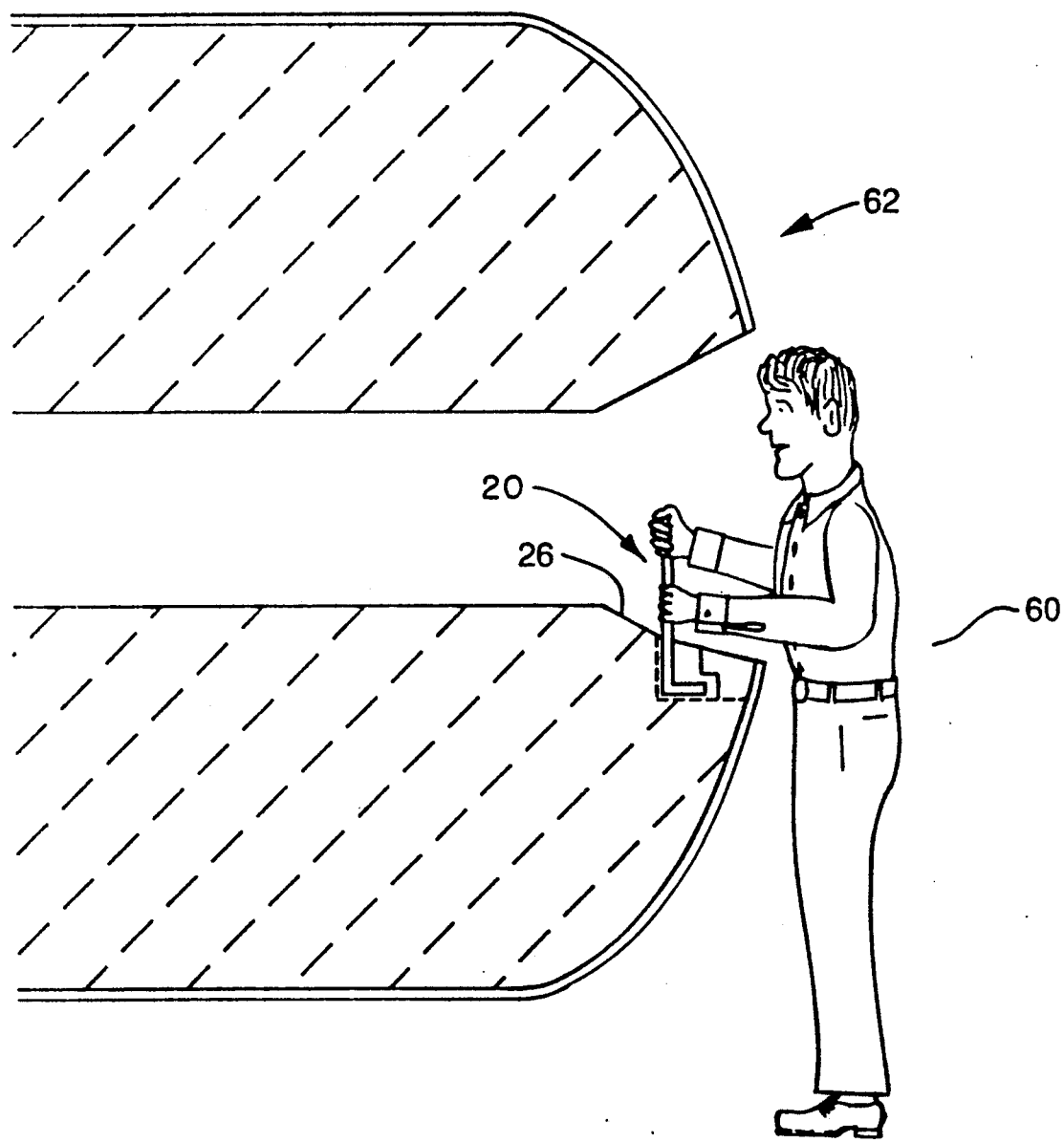
FIG. 4 is a partial sectional elevation view of solid material for cutting by the tool embodying the present invention.

The so-sharpened outside edges, provide a ramp into the opening of the cutting head 28 and direct a cutting or shaving of the solid material being cut, through such opening, as indicated in FIGS. 3 and 4. Further the so-sharpened outside cutting head edges permit a reduced angle of initial incision and a gain of mechanical advantage for such incision.

Figure 5:
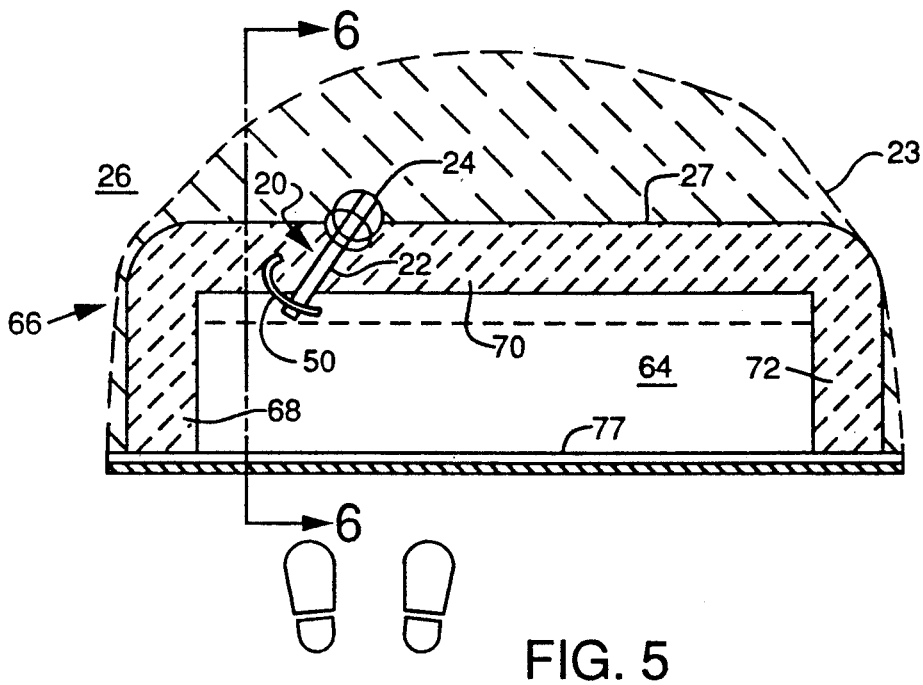
FIG. 5 is a plan view of the solid material cutting tool of the invention in operation.
Figure 6:
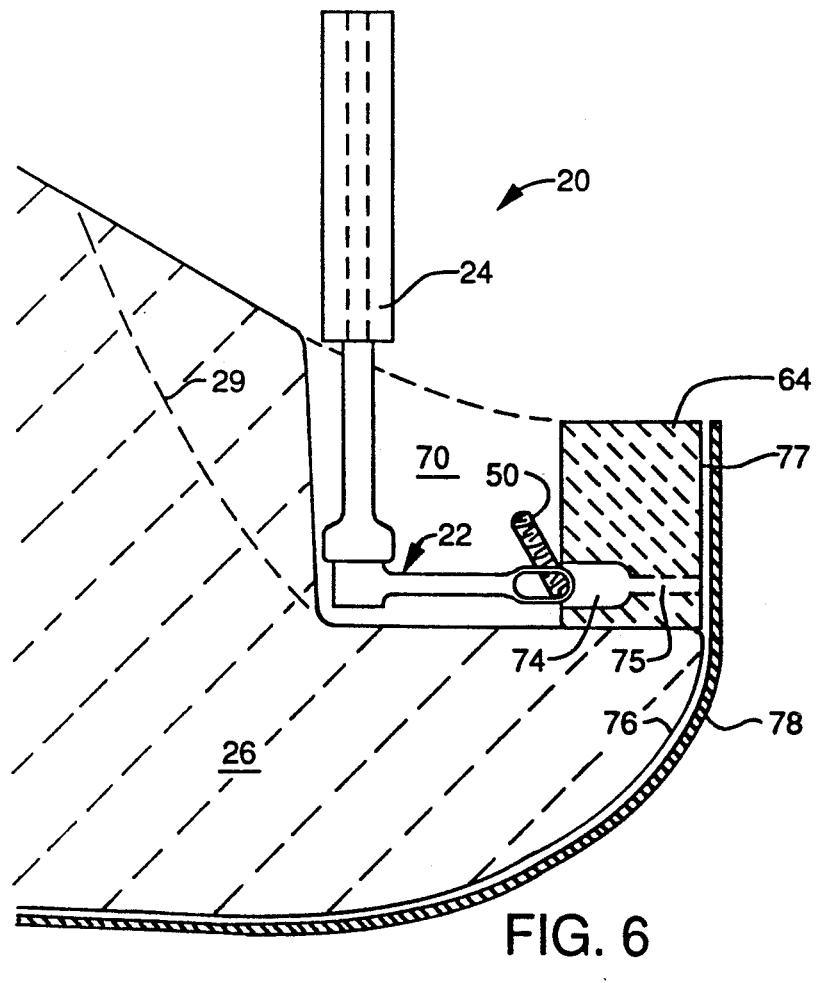
FIG. 6 is an elevation view of the cutting tool of FIG. 5 in operation, taken on lines 6–6, looking in the direction of the arrows.

In a preferred design, the rounded edge 42 of the cutting head 28 is thicker than its adjoining side walls 38, as shown in FIG. 8. Such added thickness of the rounded blade portion, serves to impart a curl to the solid material cutting passing through the opening 44 thereof so that such cutting 50 can be readily seen, grabbed and removed even during an undercutting step, as indicated in FIGS. 5 and 6. For example, the cutting tool can be machined from a 5/16" tool steel square rod with the parallel edges of such square rod being joined by a radial curve. The radial end is then machined with an elongated rounded, aperture therethrough. The aperture is positioned e.g., 0.050" from the radial end of such cutting head and a 0.035" distance from the parallel edges of such head, for about 1/4" of elongation. The outside cutting edges are sharpened, as described above and illustrated e.g., in FIGS. 7 and 10.

Sharpening the opposed pair of outside edges of the cutting tool, allows for cutting the solid material in two directions (for maximum stroke efficiency) while the slightly thicker radial portion of the cutting head, directs the excised cuttings or shavings in a backward curl, creating easier cutting removal during the cutting operation, particularly during the undercutting operation more fully discussed below.

In operation, the worker 60 approaches the after end of a rocket 62 and commences excavation in the solid propellant 26, to excise a sample of such propellant 64, as shown in FIGS. 3 4, 5 and 6.

Initially the operator 60, employs just the straight section of the tool assembly i.e. solid material cutting tool 22 to excavate the channel 66, having paths 68, 70 and 72, to define the shape of the sample 64, as shown in FIG. 5. As the channel 66 gets deeper, the operator can, if desired, attach the cutting tool 22 to a handle axially aligned therewith (not shown).

When the channel is sufficiently deep e.g., about 2½", the sample can then be undercut for removal. That is, the cutting tool 22 is mounted at an angle to an adjustable-length handle 24, e.g., as shown in FIG. 6 and the operator commences to carve a channel 74 under the sample 64, as shown in FIG. 6.

When the channel 74 is of sufficient depth for pivoting purposes, the operator may switch to a smaller sized tool like 22 (not shown) and continue to carve a considerably smaller channel 75 under such sample (and thus generate less scrap propellant material) until such smaller cutting tool cuts a channel 75 proximate the rocket liner or boot 76 and metal casing 78, as indicated in FIG. 6.

The operator then removes the cutting assembly 20 from the cut channels 75, 74 and 70, replaces the cutting tool (similar to cutting tool 22) with a straight blade 80, shown in FIG. 11, by mounting the latter cutting blade on the adjustable handle 24 and reinserts such straight cutting blade 80, into the channels 70, 74 and 75, (as shown in FIGS. 5 and 6) so as to slice through the boot 76 but not the metal casing 78.

The operator the cuts through the boot 76, uhderneath the sample 64 and up both ends thereof, to remove such sample 64 and the attached boot segment 77 as shown or indicated in FIGS. 5 and 6.

The sample can then be taken to e.g., laboratory for testing as to the stability of the propellant material, its adhesion to the boot and other tests of its condition.

The tool components can be of different sizes, as indicated above, depending upon the application. Thus a larger cutting tool 22 is employed in making the initial excavations for sample removal, e.g., a cutting head of at least ½" in width, is employed for cutting the channels 68, 70 and 72. For undercutting the excavated sample, a smaller cutting head is desirably employed, e.g., a head ⅜" wide followed by a head ¼" wide, after which the boot is sliced to free the so-cut sample, as described above.

Thus various sized solid material cutting heads can be employed to cut solid material as desired, within the scope of the invention. Such cutting tools can, as noted above, be employed without a handle, mounted in alignment with a handle or at an angle thereto. The cutting head of the invention can have but one blade which wraps around an opening but preferably has a pair of opposed cutting edges so that cutting of solid material can take place on forward and backward strokes of cutting head into the material, thus speeding the cutting process.

The cutting tool blade desirably operates at but at a slight angle to the surface of the channel being cut, i.e. with the tool stem 30 being nearly normal thereto so as to cut with relatively long and level strokes therein. However, such cutting tool can operate at any desired cutting angle to the material being cut.

The cutting tool of the invention, in excavating and undercutting a sample of solid material, considerably reduces waste or scrap material over that generated by prior art tools. That is, excess scrap material generated by prior art tools, is shown in the area defined between lines 23 and 27 of FIG. 5 as well as indicated by line 29 in FIG. 6. The so-bounded propellant material previously lost, is now conserved by the cutting tool 22 and handle 24 embodying the invention.

Accordingly, the tool of the invention is employed to excavate or cut channels around a sample and then undercut such sample to free same.

Thus the cutting tool embodying the present invention cuts uniform solid material cuttings or shavings and practically eliminates all dust related to such cutting procedure. It makes the process of undercutting e.g. the propellant sample, less time consuming, less wasteful and considerably safer e.g., due to the reduced amount of propellant dust in such cutting.

The cutting tool embodying of the invention can be made of various rigid materials, e.g., metal such as stainless steel. For cutting inflammable material, including solid rocket materials, such cutting tool should be formed of a non-sparking, conductive material. Except for the cutting edges and fixture mount, the rest of the tool surface can be bonded with a low friction, non-static material such as "Teflon." Further, such cutting tool can be electrically grounded through the handle mount, where the material to be cut is inflammable or explosive.

The cutting head of the cutting tool of the invention can be shaped in various shapes other than rounded and/or U-shaped, as desired, such as triangular, rectangular, pentagonal, circular, oval, rounded angular, or a combination thereof as desired, within the scope of the invention.

The cutting tool of the invention can be hand-held, for operation, mounted on a handle at various angles or mounted on other mechanical arms fixtures and the like.

The cutting tool of the invention is suitable for mounting on extension arms and operating by remote control by operators or by computer robotic technology and the like, as desired within the scope of the invention. Further, as noted above, the cutting tool of the invention is suitable for cutting a variety of solid materials in addition to rocket propellant, within the scope of the invention.

However the cutting tool of the invention effectively promotes the removal of relatively large propellant samples from solid rocket motors, with improved safety, reduced material waste and with reduced worktime.

What is claimed is:

1. A tool for cutting solid material comprising, a handle, a blade mounted to said handle, said blade having at least two sidewalls joined by an endwall, which walls define an opening with at least a portion of the cutting edge of said blade pointing generally in the direction of an axis passing through said opening, the endwall being thicker than either of said sidewalls, said blade having an inside beveled edge so as to direct a cutting from said material through said opening and upwardly for removal.

2. The tool of claim 1 wherein said blade sides bend at least partially around said opening to define a channel-shaped blade.

3. The tool of claim 1 wherein said blade is curved side-wise to define a sleeve, an edge of which is a cutting edge.

4. The tool of claim 3 wherein said blade has a pair of spaced cutting edges, defining opposite edges of said sleeve so that such blade can move back and forth through said material, cutting a channel therein in both directions of movement.

5. The tool of claim 4 wherein said cutting edges are beveled into said opening from the outside sleeve edge.

6. The tool of claim 3 wherein said blade is mounted to a stem, mounted in turn to said handle.

7. The tool of claim 6 wherein said stem is mounted at an angle to said handle.

8. The tool of claim 6 wherein said stem and blade are detachable from said handle and replaceable with another stem and blade of smaller sleeve width.

9. The tool of claim 8 wherein the replacement blade is a curved blade of smaller radius of curvature.

10. The tool of claim 3 wherein the blade opening is of sufficient size so that upon cutting into said material, a cutting therefrom can pass through said opening so that such blade can move back and forth through said material, cutting a channel therein in both directions of movement.

11. The tool of claim 3 wherein said blade wraps around said opening in a closed loop to define a cutting head.

12. The tool of claim 1 wherein said blade wraps around said opening to define a U-shaped cutting edge.

13. The tool of claim 1 wherein said blade has rounded ends joined by elongated sidewalls to permit ready passage of a cutting therethrough.

14. The tool of claim 1 wherein said blade wraps around said opening in a rounded shape.

* * * * *